US009247917B2

(12) United States Patent
Kodaira

(10) Patent No.: US 9,247,917 B2
(45) Date of Patent: Feb. 2, 2016

(54) X-RAY COMPUTED TOMOGRAPHY APPARATUS

(71) Applicants: KABUSHIKI KAISHA TOSHIBA, Minato-ku (JP); Toshiba Medical Systems Corporation, Otawara-shi (JP)

(72) Inventor: Yasuo Kodaira, Utsunomiya (JP)

(73) Assignees: KABUSHIKI KAISHA TOSHIBA, Minato-ku (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/730,945

(22) Filed: Jun. 4, 2015

(65) Prior Publication Data

US 2015/0265232 A1 Sep. 24, 2015

Related U.S. Application Data

(63) Continuation of application No. PCT/JP2013/082628, filed on Dec. 4, 2013.

(30) Foreign Application Priority Data

Dec. 4, 2012 (JP) .................................. 2012-265648
Dec. 4, 2013 (JP) .................................. 2013-250907

(51) Int. Cl.
*H05G 1/02* (2006.01)
*A61B 6/00* (2006.01)

(52) U.S. Cl.
CPC ................ *A61B 6/4488* (2013.01); *A61B 6/44* (2013.01); *A61B 6/4447* (2013.01); *A61B 6/4476* (2013.01)

(58) Field of Classification Search
CPC ............ A61B 6/02; A61B 6/03; A61B 6/032; A61B 6/035; A61B 6/44; A61B 6/4429; A61B 6/4435; A61B 6/4447; A61B 6/4488; A61N 5/10; A61N 5/1077; A61N 5/1081; A61N 5/1082; F24F 7/00; F24F 7/007; F24F 7/013; F24F 7/02; F24F 7/025; F24F 13/00; F24F 13/20; F24F 2007/001; F24F 2013/205; F01P 1/00; F01P 1/06; F01P 1/08; F01P 3/00; F01P 3/12; F01P 3/14; F01P 5/02; F01P 5/06; F01P 7/00; F01P 7/02; F01P 9/00; F01P 9/04; F01P 11/00; F01P 11/10
USPC ............. 378/4, 141, 189, 193, 197–200, 204, 378/210; 454/184–186, 237, 239, 241, 251, 454/253, 254, 256, 261, 262, 269, 275, 338, 454/339, 341, 367
See application file for complete search history.

(56) References Cited

U.S. PATENT DOCUMENTS 5,761,269 A * 6/1998 Sugihara ............... A61B 6/4488 378/199
6,491,428 B1 * 12/2002 Takanashi ............... A61B 6/035 378/199

(Continued)

FOREIGN PATENT DOCUMENTS

JP 07-194587 A 8/1995
JP 09-313474 A 12/1997

(Continued)

OTHER PUBLICATIONS

International Search Report issued Mar. 11, 2014 in PCT/JP2013/082628 filed Dec. 4, 2013.

(Continued)

*Primary Examiner* — Anastasia Midkiff
(74) *Attorney, Agent, or Firm* — Oblon, McClelland, Maier & Neustadt, L.L.P.

(57) ABSTRACT

An X-ray tube and An X-ray detector are mounted on a gantry rotating unit. A gantry fixing unit supports the gantry rotating unit so as to allow it to rotate about a rotation axis. A cover covers the gantry rotating unit and the gantry fixing unit. At least one outlet for discharging air inside the gantry is formed in the cover at a position shifted from an area squaring facing the outer circumference of the gantry rotating unit along the rotation axis. At least one cooling fan is mounted on the gantry fixing unit so as to be located near at least one outlet, and sends air to at least one outlet.

5 Claims, 10 Drawing Sheets

(56) References Cited

U.S. PATENT DOCUMENTS

| | | | |
|---|---|---|---|
| 7,311,439 B2* | 12/2007 | Muller | A61B 6/035 378/15 |
| 8,282,278 B2* | 10/2012 | Sharpless | A61B 6/035 378/199 |
| 2002/0009174 A1* | 1/2002 | Sasaki | A61B 6/035 378/4 |
| 2004/0114723 A1* | 6/2004 | Ray | A61B 6/4488 378/141 |
| 2009/0232281 A1* | 9/2009 | Jimbo | A61B 6/035 378/199 |
| 2009/0279660 A1* | 11/2009 | Takamatsu | A61B 6/4488 378/19 |
| 2010/0177863 A1* | 7/2010 | Jimbo | A61B 6/035 378/15 |
| 2014/0169531 A1* | 6/2014 | Kodaira | A61B 6/4488 378/196 |

FOREIGN PATENT DOCUMENTS

| | | |
|---|---|---|
| JP | 2001-137224 A | 5/2001 |
| JP | 2002-345804 A | 12/2002 |
| JP | 2010-227382 A | 10/2010 |
| JP | 2011-143063 A | 7/2011 |

OTHER PUBLICATIONS

International Written Opinion issued Mar. 11, 2014 in PCT/JP2013/082628 filed Dec. 4, 2013 with English translation.

* cited by examiner

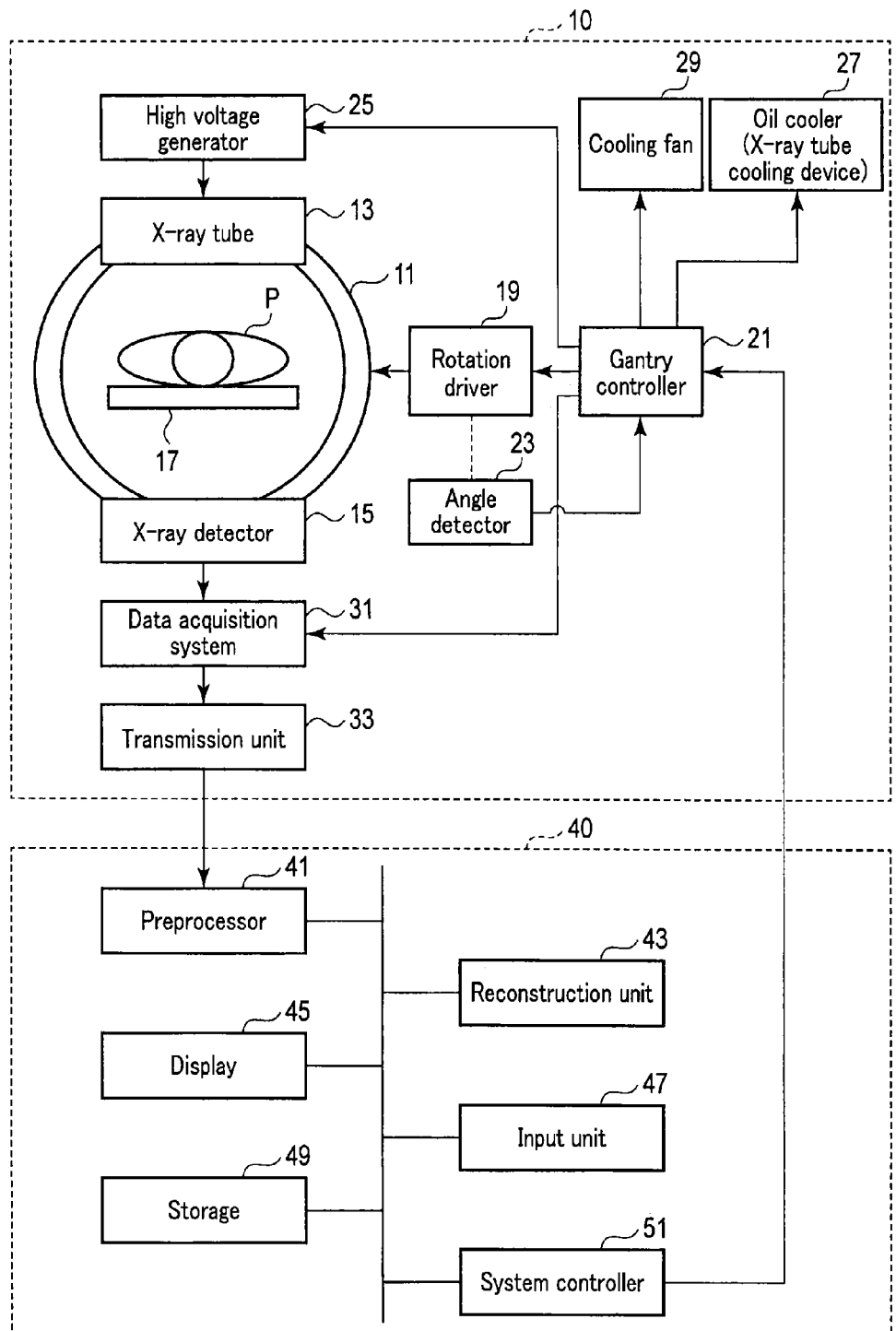
F I G. 1

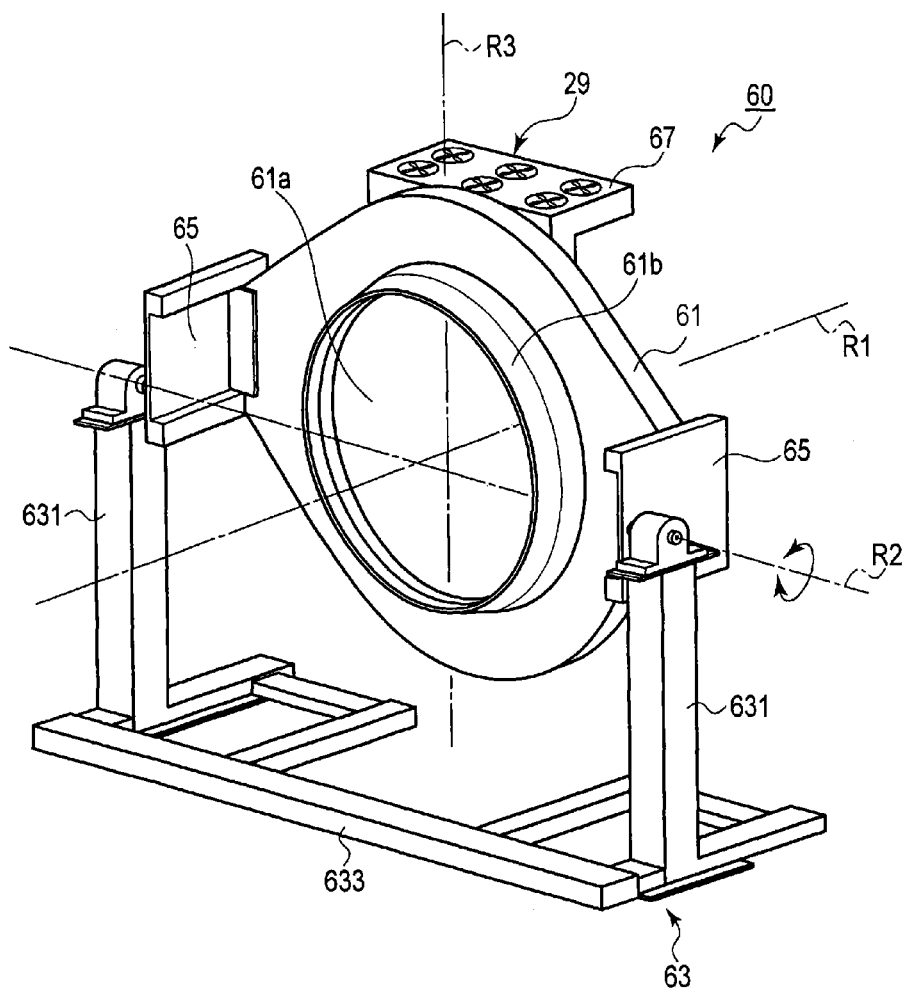
F I G. 4

X-RAY COMPUTED TOMOGRAPHY APPARATUS

CROSS-REFERENCE TO RELATED APPLICATIONS

This application is a Continuation application of PCT Application No. PCT/JP2013/082628, filed Dec. 4, 2013 and based upon and claims the benefit of priority from the Japanese Patent Application No. 2012-265648, filed Dec. 4, 2012, and No. 2013-250907, filed Dec. 4, 2013, the entire contents of all of which are incorporated herein by reference.

FIELD

Embodiments described herein relate generally to an X-ray computed tomography apparatus.

BACKGROUND

As shown in FIG. 9, in order to shorten the startup time for scanography, the stop position of a gantry rotating unit at the waiting time (the time of stoppage of rotation) of the gantry is set to locate an X-ray tube 101 at 0° (the uppermost portion). An X-ray tube cooling device 103 is mounted next to the X-ray tube 101. The X-ray tube cooling device 103 performs cooling by circulating oil between itself and the X-ray tube 101. The X-ray tube cooling device 103 is called oil cooler. A gantry side surface cover 105 is provided with an outlet 107 to efficiently exhaust heat conducted from the oil cooler 103 to the outside of the gantry. A cooling fan 109 is provided in a local portion of the main frame near the outlet 107. The cooling fan 109 sends air inside the gantry to the outlet 107 to exhaust the air outside. As shown in FIG. 9, since the X-ray tube 101 is placed at 0° at the waiting time of the gantry, the oil cooler 103 is placed at a position shifted from 0°.

As shown in FIG. 10, a lower cover 111 is provided with an inlet 113 for sucking air into the gantry. Air with lower temperature than air inside the gantry, is sucked into the gantry through the inlet 113. The sucked air mainly flows from the inlet 113 to the outlet 107. Since the X-ray tube 101 is placed at the nearly 0° position at the waiting time of the gantry, stagnation points of air occur in portions above an X-ray detector 115 and a DAS (data acquisition system) 117 arranged to face the X-ray tube 101 through the rotation axis. This makes it difficult to cool the X-ray detector 115 and the data acquisition system 117. There is room for improvement in cooling efficiency with respect to the X-ray detector 115 and the data acquisition system 117.

In addition, as shown in FIG. 10, another outlet 119 is provided to exhaust air in an area on the opposite side to the oil cooler 103 inside the gantry in the lateral direction to the outside of the gantry. A cooling fan 121 is also provided near the outlet 119. The cooling fan 121 exhausts air in the area on the opposite side to the oil cooler 103 to the outside of the gantry. However, since the main heat source inside the gantry is the oil cooler 103, there is room for improvement in exhaust efficiency based on the cooling fan 121 as compared with the cooling fan 109.

BRIEF DESCRIPTION OF THE DRAWING

FIG. 1 is a block diagram showing the arrangement of an X-ray computed tomography apparatus according to an embodiment.

FIG. 4 is a schematic perspective view of a gantry fixing unit in FIG. 2.

DETAILED DESCRIPTION

Figure 2:
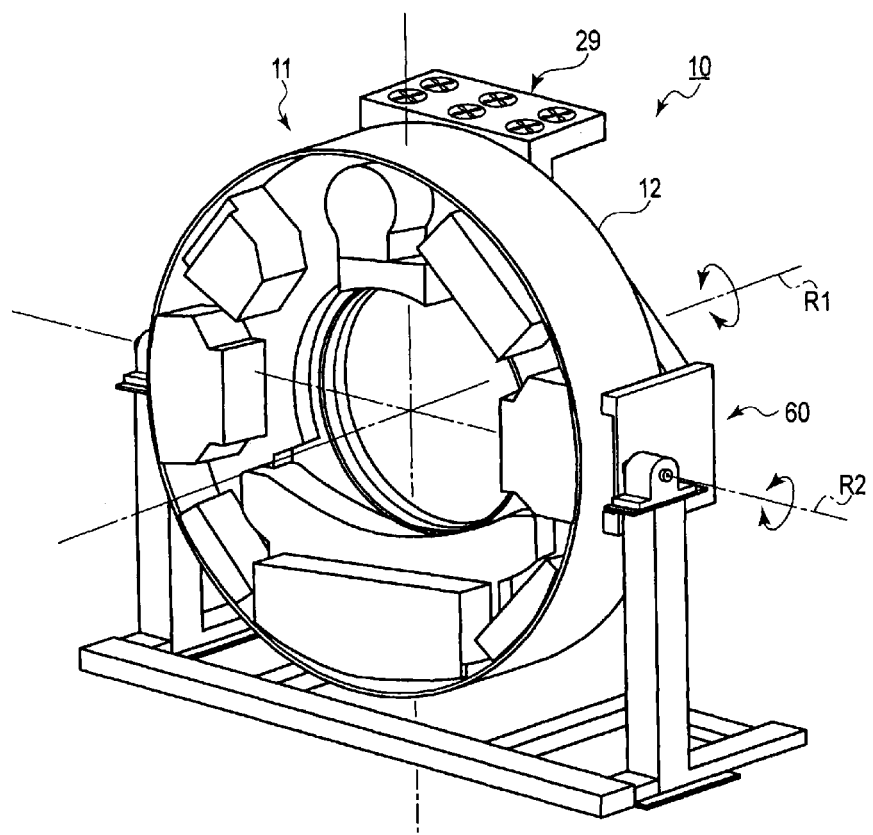
FIG. 2 is a schematic perspective view of a gantry in FIG. 1.

In general, according to one embodiment, an X-ray computed tomography apparatus includes an X-ray tube, an X-ray detector, a rotating unit, a fixing unit, a cover, and at least one exhaust fan. The X-ray tube is configured to generate X-rays. The X-ray detector is configured to detect X-rays generated from the X-ray tube. The X-ray tube and The X-ray detector are mounted on the rotating unit. The fixing unit is provided with the rotating unit along a rotation axis direction and configured to support the rotating unit so as to allow the rotating unit to rotate about the rotation axis. The cover which covers the rotating unit and the fixing unit and has at least one outlet for discharging inside air which is formed at a position shifted from an area along the rotation axis, the position squarely faces an outer circumference of the rotating unit. The at least one exhaust fan is mounted on the fixing unit so as to be located near the at least one outlet and configured to send air to the at least one outlet.

An X-ray computed tomography apparatus according to this embodiment will be described below with reference to the accompanying drawings.

FIG. 1 is a block diagram showing the arrangement of an X-ray computed tomography apparatus 1 according to this embodiment. As shown in FIG. 1, the X-ray computed tomography apparatus 1 includes a gantry 10 and a console 40.

The gantry 10 includes a gantry rotating unit 11 in a cover having an opening portion 11a. The gantry rotating unit 11 includes an X-ray tube 13 and an X-ray detector 15 which are arranged to face each other. An FOV (field of view) is set in the opening of the gantry rotating unit 11. A top 17 is positioned such that an imaging area of an object (patient) P is included in the FOV. The gantry rotating unit 11 is electrically connected to a rotation driver 19. The rotation driver 19 rotates the gantry rotating unit 11 at a predetermined angular velocity under the control of a gantry controller 21. An angle detector 23 such as a rotary encoder is attached to the rotation driver 19. The angle detector 23 repeatedly generates an electrical pulse signal (to be referred to as an angle signal hereinafter) corresponding to the angle of the gantry rotating unit 11 around a rotation axis R1 every time the gantry rotating unit 11 rotates through a predetermined angle. Each angle signal is supplied to the gantry controller 21.

In this case, the uppermost angle of the gantry rotating unit 11 around the rotation axis R1 is defined as 0°, and the lowermost angle is defined as 180°. The angle of the gantry rotating unit 11 around the rotation axis R1 at the time of the stoppage of rotation is called the home position.

The X-ray tube 13 generates X-rays upon receiving a high voltage from a high voltage generator 25. The high voltage generator 25 applies a high voltage to the X-ray tube 13 under the control of the gantry controller 21.

Although described in detail later, the gantry 10 incorporates an X-ray tube cooling device (oil cooler) 27 and cooling fans 29. The oil cooler 27 performs cooling by circulating oil between itself and the X-ray tube 13 under the control of gantry controller 21. Each cooling fan 29 is an exhaust fan which sends air inside the gantry 10 to the outside under the control of the gantry controller 21.

The X-ray detector 15 detects the X-rays generated from the X-ray tube 13. The X-ray detector 15 is equipped with a plurality of X-ray detection elements arrayed two-dimensionally. For example, the plurality of X-ray detection elements are arrayed along an arc centered on the rotation axis R1 of the gantry rotating unit 11. The arraying direction of the X-ray detection elements along the arc is called a channel direction. The plurality of X-ray detection elements arrayed along the channel direction are called an X-ray detection element array. A plurality of X-ray detection element arrays are arrayed along a row direction along the rotation axis R1. Each detection element detects the X-rays generated from the X-ray tube 13 and generates an electrical signal (current signal) corresponding to the intensity of the detected X-rays. The generated electrical signal is supplied to a DAS (data acquisition system) 31.

The data acquisition system 31 acquires electrical signals for each view via the X-ray detector 15 under the control of the gantry controller 21. As is well known, a view corresponds to the rotational angle of the gantry rotating unit 11 around the rotation axis R1. In addition, from the viewpoint of signal processing, a view corresponds to a data sampling point at the time of the rotation of the gantry rotating unit 11. The data acquisition system 31 converts acquired analog electrical signals into digital data. The digital data is called raw data. A noncontact type transmission unit 33 supplies the raw data to the console 40 for each predetermined view.

The gantry controller 21 comprehensively controls the respective types of devices mounted on the gantry 10 in accordance with instructions from a system controller 51 in the console 40. The gantry controller 21 controls the rotation driver 19, the high voltage generator 25, the oil cooler 27, the cooling fans 29, and the data acquisition system 31.

The console 40 includes a preprocessor 41, a reconstruction unit 43, a display 45, an input unit 47, a storage 49, and the system controller 51. The preprocessor 41 executes preprocessing such as logarithmic conversion and sensitivity correction for the raw data supplied from the transmission unit 33. The data for which the preprocessing has been executed is called projection data. The reconstruction unit 43 reconstructs image data concerning the object based on the projection data. The display 45 displays the image data generated by the reconstruction unit 43. The Input unit 47 accepts various types of commands and information inputs from the user via an input device. The storage 49 stores raw data, projection data, and image data. The storage 49 stores control programs. The system controller 51 reads out control programs stored in the storage 49 and loads them into the memory. The system controller 51 controls the respective units in accordance with the loaded control programs.

The structure of the gantry 10 according to this embodiment will be described below.

Figure 3:
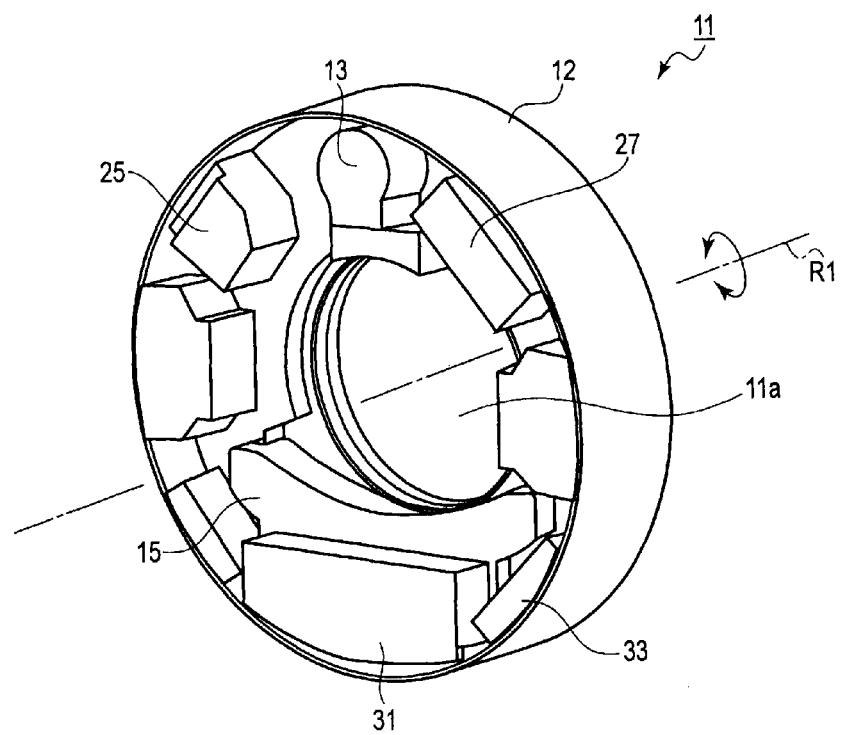
FIG. 3 is a schematic perspective view of a gantry rotating unit in FIG. 2.

FIG. 2 is a schematic perspective view of the gantry 10. Note that FIG. 2 shows the gantry 10 from which the cover is detached. As shown in FIG. 2, the gantry 10 includes the gantry rotating unit 11 and a gantry fixing unit 60. FIG. 3 is a schematic perspective view of the gantry rotating unit 11. FIG. 4 is a schematic perspective view of the gantry fixing unit 60.

As shown in FIGS. 2 and 3, the gantry rotating unit 11 includes a rotating frame 12 having a nearly cylindrical shape, with the opening portion 11*a* being formed in the center. A hole or recess portion is formed in the rotating frame 12 to mount the X-ray tube 13, the X-ray detector 15, the high voltage generator 25, the oil cooler 27, the cooling fans 29, the data acquisition system 31, the transmission unit 33, and the like. The rotating frame 12 is a metal frame formed from a metal such as aluminum. Various types of devices such as the X-ray tube 13, the X-ray detector 15, the high voltage generator 25, the oil cooler 27, the cooling fans 29, the data acquisition system 31, and the transmission unit 33 operate upon receiving power from the gantry controller 21 (not shown) provided on the gantry fixing unit 60. The X-ray tube 13 and the X-ray detector 15 are mounted on the rotating frame 12 so as to face each other through the opening portion 11*a*. The oil cooler 27 is connected to the X-ray tube 13 via an oil flow path (not shown). The oil circulates between the X-ray tube 13 and the oil cooler 27 via this flow path. The oil cooler 27 sucks the oil heated by the X-ray tube 13, cools the sucked oil, and supplies the cooled oil to the X-ray tube 13 via the flow path. The oil cooler 27 cools the X-ray tube 13 by circulating the oil. Although not shown, the oil cooler 27 is provided with an inlet (to be referred to as an oil cooler inlet hereinafter), an outlet (to be referred to as an oil cooler outlet hereinafter), and a fan (to be referred to an oil cooler cooling fan hereinafter). The oil cooler 27 draws up air inside the gantry 10 by using the oil cooler cooling fan, and sucks the drawn air from the oil cooler inlet. The sucked air cools the oil cooler 27. The air sucked by the oil cooler 27 is discharged from the oil cooler outlet into the gantry 10.

As shown in FIG. 4, the gantry fixing unit 60 includes a main frame 61, a base stand 63, and gantry arms 65. The main frame 61 supports the gantry rotating unit 11 so as to allow it to rotate about the rotation axis R1. The main frame 61 is a metal frame formed from a metal such as aluminum. An opening 61*a* is formed in the center of the main frame 61. A slip ring mechanism (not shown) is mounted on the inner circumferential side of an edge portion 61*b* of the opening 61*a* of the main frame 61. The main frame 61 is rotatably connected to the rotating frame 12 via a bearing and the like. Power is supplied to the respective types of devices of the gantry rotating unit 11 via the slip ring mechanism.

The base stand 63 is installed on the floor surface of a CT imaging room. The base stand 63 supports the main frame 61 at a distance from the floor surface. The base stand 63 includes, for example, two upright frames 631 and a connection frame 633. The two upright frames 631 are mounted on the two side surfaces of the main frame 61 and installed upright on the floor surface. The connection frame 633 connects the two upright frames 631 to strength the support of the main frame 61 by the two upright frames 631. The base stand 63 is formed from a metal such as aluminum.

The two gantry arms 65 support the main frame 61 so as to allow it to tilt around a horizontal axis R2 which is perpendicular to the rotation axis R1 and parallel to the floor surface. The two gantry arms 65 are arranged such that the gantry rotating unit 11 intersects the horizontal axis R2, and hence support the main frame 61 so as to separate it from the horizontal axis R2 in the direction of the rotation axis R1. The gantry arms 65 are mounted at the upper portions of the base stand 63 to couple the base stand 63 to the main frame 61. As the main frame 61 tilts, a vertical axis R3 perpendicular to the rotation axis R1 and the horizontal axis R2 tilts with respect to the floor surface. The gantry arms 65 tilt the main frame 61 upon receiving a driving signal from a driving device (not shown) in the cover. The gantry arms 65 are formed from a metal such as aluminum.

Figure 5:
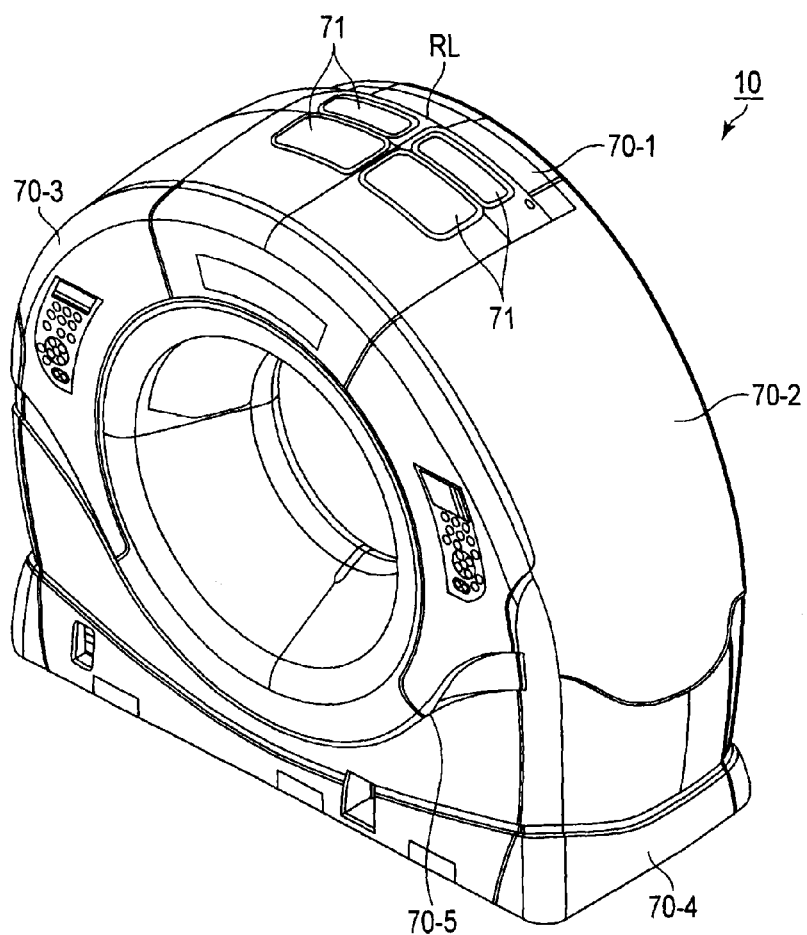
FIG. 5 is a perspective view showing the outer appearance of the gantry in FIG. 1.

FIG. 5 is a perspective view showing an outer appearance of the gantry 10. As shown in FIG. 5, the gantry rotating unit 11 and the gantry fixing unit 60 are covered by a cover 70. More specifically, the cover 70 includes an upper cover 70-1, a right surface cover 70-2, a left surface cover 70-3, a bottom cover 70-4, and a lower cover 70-5. A plurality of outlets 71 for discharging air inside the gantry are limitedly formed in a local area RL of the cover 70. The local area RL is provided at a position shifted from an area of the upper cover 70-1 which squarely faces the outer circumference of the gantry rotating unit 11 along the rotation axis R1. That is, the outlets 71 are formed at a position shifted from an area of the upper cover 70-1 which squarely faces the outer circumference of the gantry rotating unit 11 along the rotation axis R1. For example, the local area RL is a single area including the 0° position, as shown in FIG. 5. In this case, the plurality of outlets 71 are formed in the upper cover 70-1. The lower cover 70-5 is mounted to prevent the bottom portion of the gantry rotating unit 11 from being seen from outside when the gantry rotating unit 11 tilts around the horizontal axis R2. A plurality of inlets (not shown in FIG. 5) are formed in the lower cover 70-5. Outer air with lower temperature than air inside the gantry is sucked into the gantry 10 from the plurality of inlets. Air inside the gantry 10 is then discharged from the plurality of outlets 71.

At the time of the stoppage of rotation, air inside the gantry 10 can be discharged from the plurality of outlets 71 by the oil cooler cooling fan. At the time of the rotation of the gantry, however, since the temperature inside the gantry 10 becomes spatially uniform, air inside the gantry 10 cannot be discharged from the plurality of outlets 71 by the oil cooler cooling fan alone. For this reason, as shown in FIGS. 2 and 4, the plurality of cooling fans 29 are mounted on the main frame 61 separately from the oil cooler cooling fan. The plurality of cooling fans 29 are arranged near the plurality of outlets 71 to improve the discharge efficiency of air inside the gantry 10. In other words, the plurality of outlets 71 and the plurality of cooling fans 29 are mounted at almost the same angular position. When the plurality of outlets 71 are provided on the uppermost portion of the cover 70, the plurality of cooling fans 29 are arranged immediately below the plurality of outlets 71. Typically, one cooling fan 29 is provided for one discharge opening portion 71.

As shown in FIGS. 2 and 4, the plurality of outlets 71 are provided in, for example, a mount plate 67 provided on the main frame 61. The mount plate 67 extends along the rotation axis R1 in a direction opposite to the gantry rotating unit 11. The mount plate 67 may be formed separately from or integrally with the main frame 61. This makes it possible to arrange the outlets 71 from directly above the gantry rotating unit 11 along the rotation axis R1 in a direction opposite to the arrangement position of the gantry rotating unit 11. That is, the outlets 71 are arranged at a position shifted from the outer circumference of the gantry rotating unit 11. This structure allows the gantry 10 as a whole to have a diameter closer to that of the rotating frame 12 than when the cooling fans 29 are provided on the outer circumference of the gantry rotating unit 11 as in the related art. This makes it possible to design the gantry 10 having a smaller size. In addition, at the time of the rotation of the gantry, the rotation of the gantry rotating unit 11 and the driving of the oil cooler 27 generate very large noise. The plurality of outlets 71 according to this embodiment are relatively spaced apart from the gantry rotating unit 11 and the oil cooler 27 as main sound sources as compared with the related art in which the plurality of outlets are formed in the outer circumference of the gantry rotating unit. Therefore, noise in the gantry 10 according to this embodiment is reduced at the time of the rotation of the gantry as compared with the related art.

Even at the time of the stoppage of rotation of the gantry rotating unit 11, it is necessary to cool the oil cooler 27. In order to efficiently cool the oil cooler 27, the gantry controller 21 places the oil cooler 27 at the nearly 0° position at the time of the stoppage of rotation of the gantry rotating unit 11. Positioning control of the oil cooler 27 will be described below.

Figure 6:
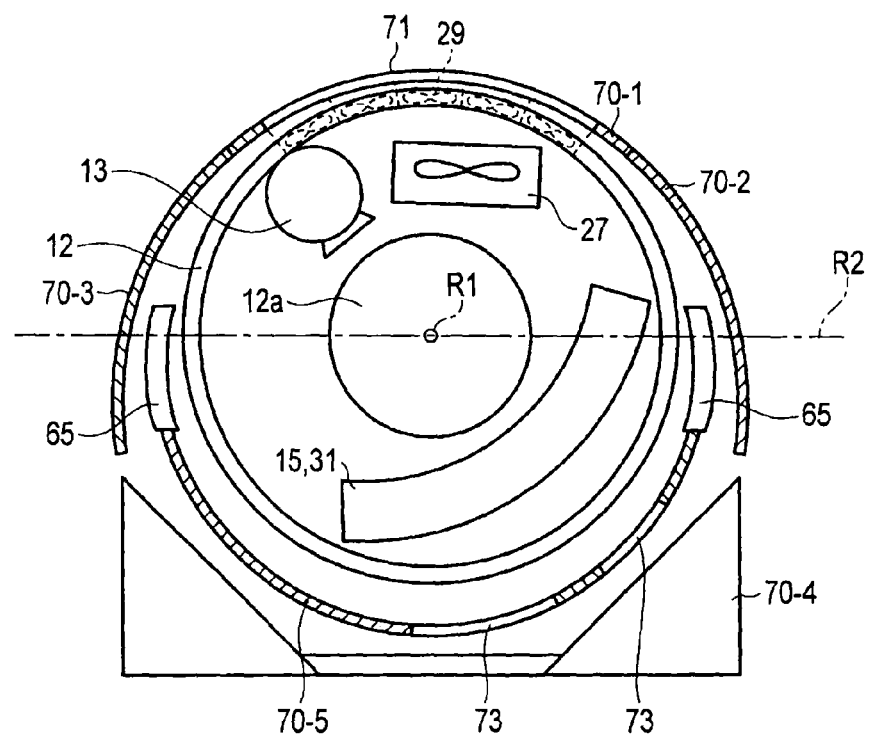
FIG. 6 is a schematic plan view showing the gantry in FIG. 1 when viewed from the front.

FIG. 6 is a schematic plan view showing the gantry 10 when viewed from the front. As shown in FIG. 6, the plurality of outlets 71 and the plurality of cooling fans 29 are provided together at the 0° position. More specifically, the plurality of outlets 71 are formed in the local area located at the uppermost portion of the upper cover 70-1. The plurality of cooling fans 29 are mounted on the main frame 61 near the plurality of outlets 71. In other words, the plurality of cooling fans 29 are arranged at the nearly 0° position. At the time of the stoppage of rotation, the oil cooler 27 is arranged at the nearly 0° position. As the oil cooler 27 is arranged at the nearly 0° position, the X-ray detector 15 is arranged at a position shifted from nearly 180°. The lower cover 70-5 is mounted below the rotating frame 12 of the gantry rotating unit 11 so as to cover the gantry rotating unit 11. Inlets 73 are formed in the lower cover 70-5.

The gantry controller 21 controls the rotation driver 19 to stop the rotation of the gantry rotating unit 11 in response to the issuance of an instruction to stop rotating the gantry 10. A rotation stop instruction may be manually issued by the user via the Input unit 47 or automatically issued from the system controller 51 in accordance with a scan sequence. When controlling to stop the rotation of the gantry rotating unit 11, the gantry controller 21 controls the rotation driver 19 to stop the reference position of the oil cooler 27 at 0°. The reference position of the oil cooler 27 can be set to an arbitrary position such as a central point or end point of the oil cooler 27 in a circumferential direction around the rotation axis R1. When the oil cooler 27 is stopped at 0°, the X-ray tube 13 is arranged at a position shifted from 0°, and the X-ray detector 15 is stopped at a position shifted from 180°, as shown in FIG. 6.

Note that, as shown in FIG. 6, the right gantry arm 65 is arranged between the right surface cover 70-2 and the rotating frame 12, and the left gantry arm 65 is arranged between the left surface cover 70-3 and the rotating frame 12. Each gantry arm 65 according to this embodiment has an arcuated shape along the circumferential shape of the rotating frame 12. This can narrow the spaces between the side surface covers 70-2 and 70-3 and the rotating frame 12 as much as possible, thus reducing the outer size of the gantry 10. In addition, as described later, it is possible to make it difficult for air to pass through the spaces between the side surface covers 70-2 and 70-3 and the rotating frame 12 by narrowing the spaces as much as possible.

Figure 7:
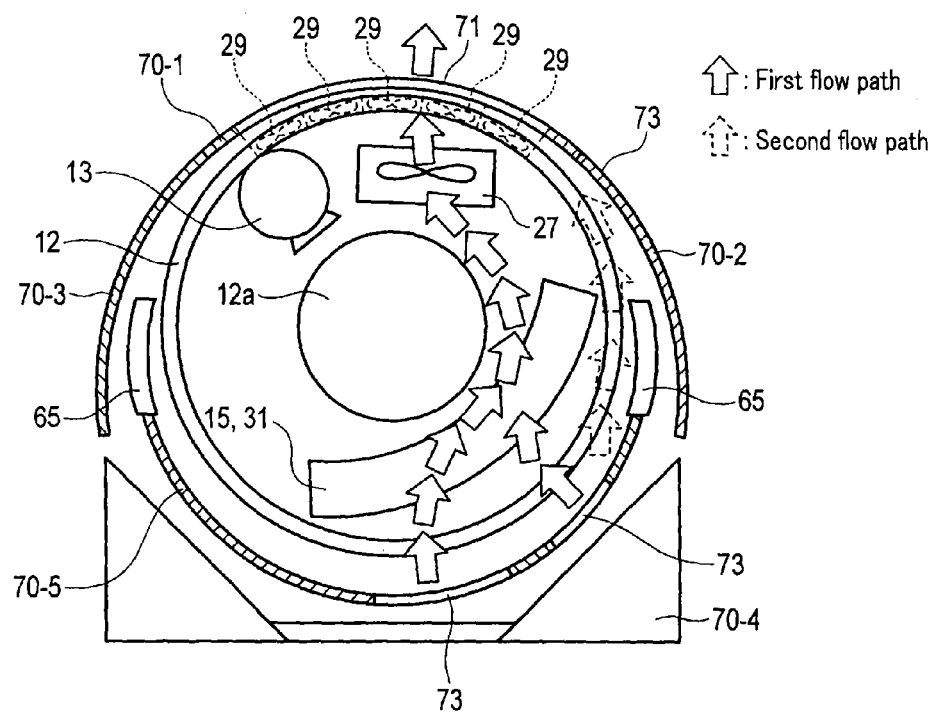
FIG. 7 is a schematic plan view showing the gantry in FIG. 1 when viewed from the front, with the flows of air being indicated by arrows.
Figure 8:
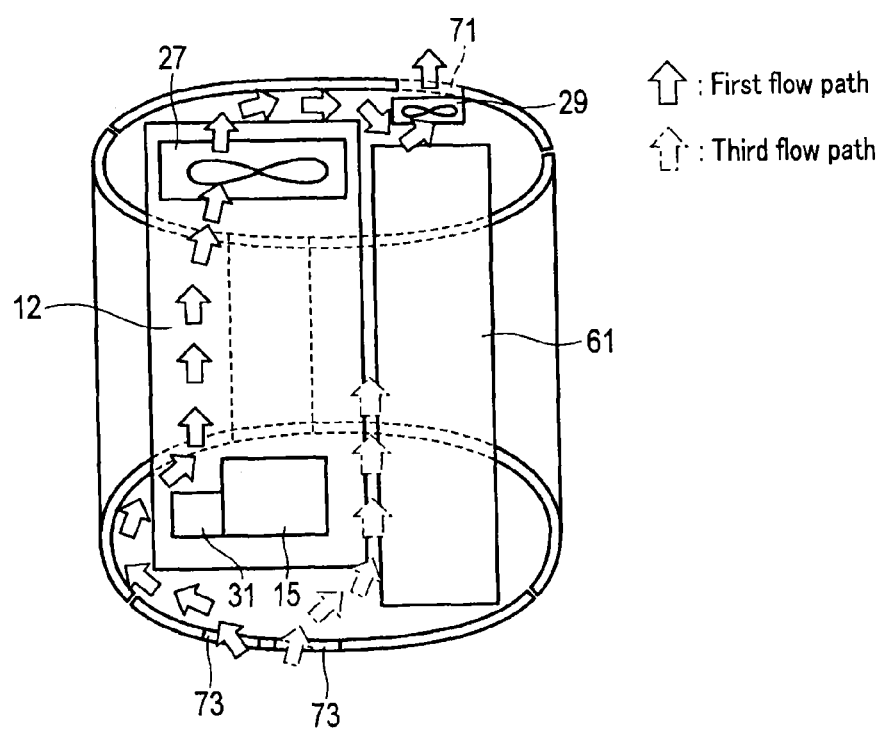
FIG. 8 is a schematic plan view showing the gantry in FIG. 1 when viewed from above the side surface side, with the flows of air being indicated by arrows.
Figure 9:
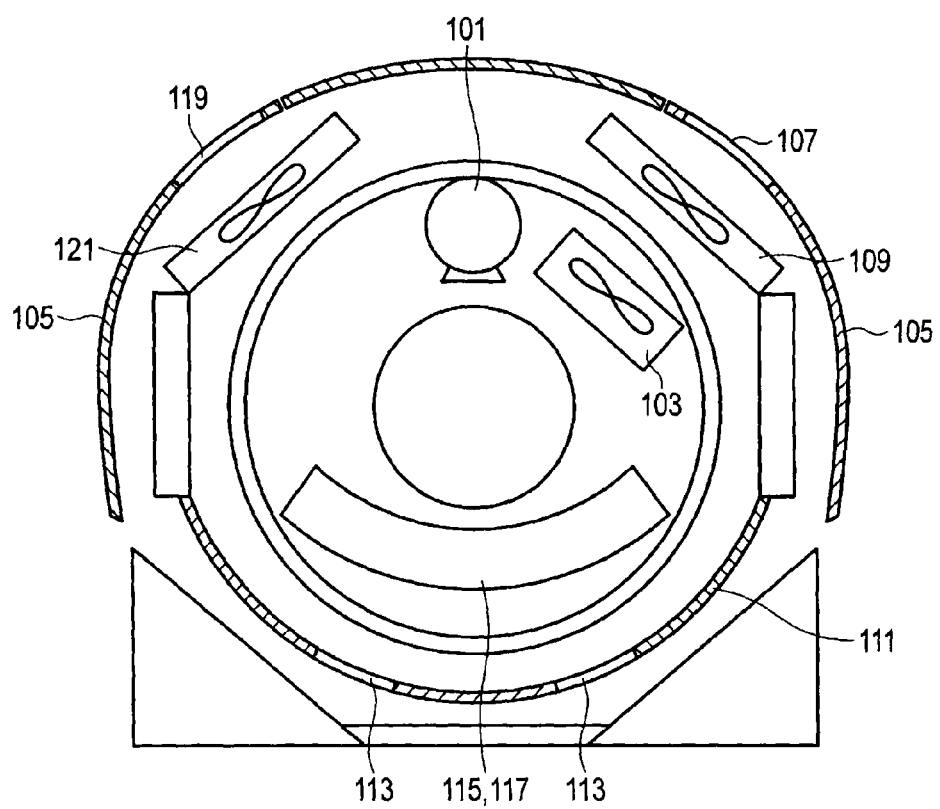
FIG. 9 is a schematic plan view showing a gantry according to the related art when viewed from the front.
Figure 10:
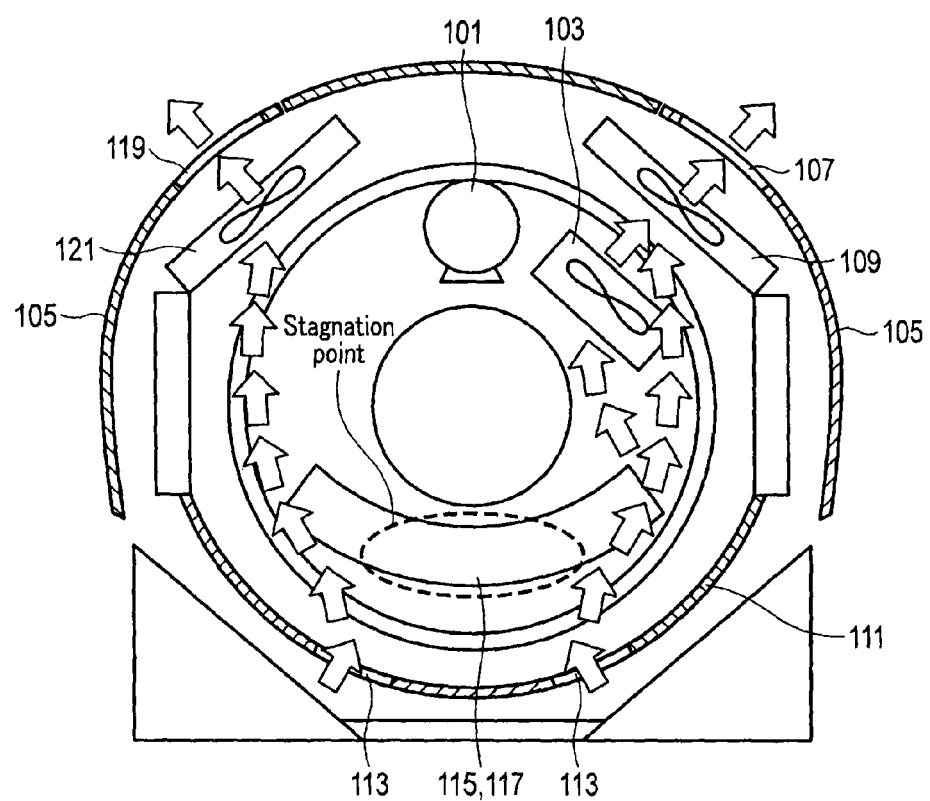
FIG. 10 is a schematic plan view showing the gantry according to the related art when viewed from the front, with the flows of air being indicated by arrows.

The flows of air at the time of the stoppage of rotation of the gantry 10 according to this embodiment will be described next. FIG. 7 is a schematic plan view showing the gantry 10 when viewed from the front, with the flows of air being indicated by arrows. FIG. 8 is a schematic plan view showing the gantry 10 when viewed from above the side surface side, with the flows of air being indicated by arrows. Referring to FIGS. 7 and 8, the flows of air are indicated by the arrows.

As shown in FIGS. 7 and 8, first of all, air lower in temperature than air inside the gantry 10 is sucked from the plurality of inlets 73 of the lower cover 70-5 into the gantry 10. The air entering the gantry 10 flows in a plurality of flow paths constructed in the gantry 10. The flow paths inside the gantry 10 are roughly classified into three types. The first flow path (the solid line arrows) passes through the X-ray detector 15 and the data acquisition system 31, extends upward along the opening portion 11a, and reaches the oil cooler inlet of the oil cooler 27. The second flow path (dotted line arrows) passes between a side surface of the rotating frame 12 and the gantry fixing unit 60 or near them, and extends upward along side surface covers 70-2 and 70-3. Note that, as described above, the gaps between the rotating frame 12 and the side surface covers 70-2 and 70-3 are designed to be narrowed as much as possible by, for example, forming the gantry arms 65 into arcuated shapes. That is, the second flow path is narrower than the first flow path. The third flow path (one-dot dashed line arrows) is a flow path extending upward in the gap between the rotating frame 12 and the main frame 61. From the viewpoint of reducing the size of the gantry, the rotating frame 12 and the main frame 61 are designed to minimize the gap between the rotating frame 12 and the main frame 61 so as to prevent them from interfering each other. Therefore, the third flow path is narrower than the first flow path. As described above, the second and third flow paths are designed to be narrow as the flow paths of air. For this reason, the most major flow path among the flow paths constructed in the gantry 10 is the first flow path.

As shown in FIGS. 7 and 8, first of all, air lower in temperature than air inside the gantry 10 is sucked from the inlets 73 of the lower cover 70-5 into the gantry 10. Most of the air sucked from the inlets 73 passes through the first flow path because the second and third flow paths are narrow. As described above, as the oil cooler 27 is arranged at the 0° position, the X-ray detector 15 is arranged at a position shifted from nearly 180°. Therefore, air can easily flow above the X-ray detector 15 and no stagnation point of air easily occurs above the X-ray detector 15 as compared with the related art in which the X-ray detector is arranged at the nearly 180° position. This makes it possible to efficiently cool the X-ray detector 15 and the data acquisition system 31. Air flowing upward along the first flow path is drawn upward by the oil cooler cooling fan via the oil cooler inlet of the oil cooler 27. The air is then discharged from the oil cooler outlet to the uppermost portion. The discharged air is quickly discharged to the outside of the gantry 10 by the cooling fans 29 arranged near the oil cooler 27.

As described above, the gantry 10 according to this embodiment has the structure in which the plurality of outlets 71 and the plurality of cooling fans 29 are arranged together in one portion. This structure places limitation on the gantry 10 such that air is discharged from one place unlike the related art in which the plurality of outlets 71 and the plurality of cooling fans 29 are dispersed at a plurality of positions. Typically, the plurality of outlets 71 and the plurality of cooling fans 29 are provided in the uppermost portion of the gantry 10 where air can be discharged together most easily. At the time of the stoppage of rotation of the gantry rotating unit 11, the oil cooler 27 is arranged near the place where the plurality of outlets 71 and the plurality of cooling fans 29 are installed. At the time of the stoppage of rotation, therefore, it is possible to quickly discharge air heated by the oil cooler 27 from the gantry 10. In addition, the plurality of outlets 71 are provided at a position offset from the outer circumference of the gantry rotating unit 11 to the main frame 61 side from the viewpoint of reducing the size of the gantry. This makes it possible to separate the outlets 71 from the gantry rotating unit 11 and the oil cooler 27, which are the main noise sources, without degrading the cooling efficiency. This implements suppression of noise. In addition, as the size of the gantry is reduced by optimizing the structure/arrangement of the respective constituent elements of the gantry 10, it is possible to make most of air sucked into the gantry 10 flow in the first flow path. As described above, the first flow path extends through the interior of the gantry rotating unit 11 equipped with most of the main heat sources of the constituent elements included in the gantry 10. In addition, the X-ray detector 15 is shifted from the nearly 180° position. Therefore, the gantry 10 can actively send air to portions above the X-ray detector 15 and the data acquisition system 31 where stagnation points of air are formed in the related art. This can improve the cooling efficiency while achieving a reduction in the size of the gantry.

This embodiment can therefore provide the X-ray computed tomography apparatus 1 which can improve the cooling efficiency inside the gantry 10.

First Modification

According to the above description, the plurality of outlets 71 and the plurality of cooling fans 29 are provided in the gantry 10. However, this embodiment is not limited to this. For example, the single discharge opening portion 71 may be provided in a local area of the cover 70, and the single cooling fan 29 may be provided near the single discharge opening portion 71 of the main frame 61 as long as there is no problem in cooling efficiency.

Second Modification

According to the above description, the plurality of outlets 71 and the plurality of cooling fans 29 are provided, in particular, at the 0° position. However, this embodiment is not limited to this. For example, the plurality of outlets 71 and the plurality of cooling fans 29 may be provided at any positions other than the 0° position as long as there is no problem in cooling efficiency.

Third Modification

According to the above description, the plurality of outlets 71 and the plurality of cooling fans 29 are provided at a position shifted from the outer circumference of the gantry rotating unit 11 to the main frame 61 side. However, this embodiment is not limited to this. The plurality of outlets 71 and the plurality of cooling fans 29 may be provided, from the viewpoint of reducing noise, at a position shifted from the outer circumference of the gantry rotating unit 11 to the opposite side to the main frame 61.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
an X-ray tube configured to generate X-rays;
an X-ray detector configured to detect X-rays generated from the X-ray tube;
a rotating unit on which the X-ray tube and the X-ray detector are mounted;
a fixing unit provided with the rotating unit along a rotation axis direction and configured to support the rotating unit so as to allow the rotating unit to rotate about the rotation axis;
a cover which covers the rotating unit and the fixing unit and has at least one outlet for discharging inside air which is formed at a position shifted from an area along the rotation axis, the position squarely faces an outer circumference of the rotating unit; and
at least one exhaust fan mounted on the fixing unit so as to be located near the at least one outlet and configured to send air to the at least one outlet.

2. The X-ray computed tomography apparatus of claim 1, wherein the at least one outlet is concentrated at an uppermost portion of the cover.

3. The X-ray computed tomography apparatus of claim 1, wherein the at least one outlet is provided at a position shifted along the rotation axis, from directly above the rotating unit to directly above the fixing unit.

4. The X-ray computed tomography apparatus of claim 1, further comprising:
a cooling device mounted on the rotating unit and configured to cool the X-ray tube;
a driver configured to generate motive power for rotating the rotating unit about the rotation axis; and
a controller configured to control the driver to locate the cooling device near the at least one outlet or the at least one exhaust fan at the time of the stoppage of rotation of the rotating unit.

5. The X-ray computed tomography apparatus of claim 1, further comprising a gantry arm covered by the cover and configured to support the fixing unit so as to allow the fixing unit to tilt around a horizontal axis perpendicular to the rotation axis,
the gantry arm having an arcuated shape along an outer circumferential shape of the rotating unit.

* * * * *